US010099967B2

(12) United States Patent
McCrary et al.

(10) Patent No.: US 10,099,967 B2
(45) Date of Patent: Oct. 16, 2018

(54) HYPERGOLIC SALTS WITH BORANE CLUSTER ANIONS

(71) Applicant: Board of Trustees of The University of Alabama, Tuscaloosa, AL (US)

(72) Inventors: Parker D. McCrary, Tuscaloosa, AL (US); Robin D. Rogers, Tuscaloosa, AL (US)

(73) Assignee: The Board of Trustees of The University of Alabama, Tuscaloosa, AL (US)

( * ) Notice: Subject to any disclaimer, the term of this patent is extended or adjusted under 35 U.S.C. 154(b) by 201 days.

(21) Appl. No.: 14/310,375

(22) Filed: Jun. 20, 2014

(65) Prior Publication Data

US 2014/0373984 A1    Dec. 25, 2014

Related U.S. Application Data

(60) Provisional application No. 61/837,404, filed on Jun. 20, 2013.

(51) Int. Cl.
| | | |
|---|---|---|
| *C06B 43/00* | (2006.01) | |
| *C07F 5/02* | (2006.01) | |
| *C06B 47/10* | (2006.01) | |

(52) U.S. Cl.
CPC .............. *C06B 43/00* (2013.01); *C06B 47/10* (2013.01); *C07F 5/027* (2013.01); *Y02P 20/542* (2015.11)

(58) Field of Classification Search
CPC .................................................... C06B 43/00
See application file for complete search history.

(56) References Cited

U.S. PATENT DOCUMENTS

| | | | | |
|---|---|---|---|---|
| 3,013,041 A | * | 12/1961 | Aftandilian | C07F 9/02 556/8 |
| 3,040,055 A | * | 6/1962 | Fetter | C07F 5/006 149/22 |
| 3,050,361 A | | 8/1962 | Muetterties | |
| 3,268,560 A | * | 8/1966 | Heying | C01B 6/00 549/213 |
| 3,309,248 A | * | 3/1967 | Rausch | C06B 43/00 149/109.2 |
| 3,453,092 A | * | 7/1969 | Hawthorne | C01B 21/16 149/22 |

(Continued)

OTHER PUBLICATIONS

Back et al., Occupational Hazards of Missile Operations with Special Regard to the Hydrazine Propellants, Aviat. Space Environ. Med., 49:591-598, 1978.

(Continued)

*Primary Examiner* — Aileen B Felton
(74) *Attorney, Agent, or Firm* — Meunir Carlin & Curfman LLC

(57) ABSTRACT

Disclosed are hypergolic salts with borane cluster anions that ignite spontaneously upon contact with nitric acid (from 70% to 100% in water) with short ignition delay. The salts, when added as trigger additive to combustible solvent or ionic liquids, make the resulting formulation hypergolic. The salts with borane cluster anions also shorten ignition delay in hypergols, such as RP-1, and additionally allow nitric acid to be used to replace liquid oxygen as an oxidizer. In some examples, the borane salts are formed in situ in an ionic liquid.

18 Claims, 6 Drawing Sheets

A

B

C

D

(56) References Cited

U.S. PATENT DOCUMENTS

| | | | | |
|---|---|---|---|---|
| 3,613,371 | A | * 10/1971 | Edwards | C06B 47/10 149/22 |
| 3,967,989 | A | 7/1976 | Hawthorne | |
| 3,971,681 | A | * 7/1976 | Rains | C06B 43/00 149/100 |
| 8,034,202 | B1 | * 10/2011 | Hawkins | C06B 47/02 149/1 |
| 2005/0022911 | A1 | * 2/2005 | Rusek | C06D 5/08 149/1 |
| 2005/0269001 | A1 | * 12/2005 | Liotta | C06B 25/34 149/1 |
| 2012/0024437 | A1 | * 2/2012 | Nicolich | C06B 21/005 149/92 |

OTHER PUBLICATIONS

Benjamin et al., Communications to the Editor, J. Am. Chem. Soc. 85:2674-2675, 1963.

Bould et al., Structural Chemistry of arachno-Nonaboranes, J. Am. Chem. Soc., 124:7429-7439:2002.

Chin et al., Infrared Spectroelectrochemistry of Boron-Hydrogen Stretches: A Tool for Diagnosis of Delocalization in Mixed-Valent Metallacarborane Complexes, J. Am. Chem. Soc., 116:9359-9360, 1994.

Chingin et al., Generation of Melamine Polymer Condensates upon Hypergolic Ignition of Dicyanamide Ionic Liquids, Angew. Chem. Int. Ed., 50:8634-8637, 2011.

Emel'Yanenko et al.,Teh Gaseous Enthalpy of Formation of the Ionic Liquid 1-Butyl-3-methylimidazolium Dicyanamide from Combustion Calorimetry, Vapor Pressure Measurements, and Ab lnitio Calculations, J. Am. Chem. Soc., 129:3930-3937, 2007.

Gao et al., Ionic liquid solubilized boranes as hypergolic fluids, J. Mater. Chem., 22:11022-11025, 2012.

Greenwood et al., Crystal Structure of Caesium Tetradecahydrononaborate(1-), CsB9H14, J. Chem. Soc., Dalton Trans., 986-989, 1972.

Hawthorne et al., Deuterium Exchange of Decaborane with Deuterium Oxide and Deuterium Chloride, J. Am. Chem. Soc., 80:754-754, 1958.

Hawthorne et al., Salts which Contain the B10H18 Anion, J. Am. Chem. Soc., 82:1825-1829, 1960.

He et al., Nitrocyanamide-Based Ionic Liquids and Their Potential Applications as Hypergolic Fuels, Chem. Eur. J., 16:5736-5743, 2010.

Hofmann et al., Structures of arachno- and hypo-B10 Clusters and Stability of Their Possible Lewis Base Adducts ([B10H12]2-, [B10J12 L]2-, [B10H13]-, [B10H13 L]-, [B10H12 2L]). An ab Initio/IGLO/NMR Investigation, Inorg. Chem., 37:5557-5565, 1998.

Hofmann et al., Solid State and Solution Structures of 9-Vertex Arachno Boron Hydride Clusters, An ab Initio/IGLO/NMR Study, Inorg. Chem., 38:652-660, 1999.

Macfarlane et al., Low viscosity ionic liquids based on organic salts of the dicyanamide anion, Chem. Commun., 1430-1431, 2001.

McCrary et al., Hypergolic ionic liquids to mill, suspend, and ignite boron nanoparticles, Chem. Commun., 48:4311-4313, 2012.

McCrary et al., Graphene and Graphene Oxide Can "Lubricate" Ionic Liquids based on Specific Surface Interactions Leading to Improved Low-Temperature Hypergolic Performance, Angew. Chem. Int. Ed., 51:9784-9787, 2012.

Nicholls et al., Metabonomic Investigations into Hydrazine Toxicity in the Rat, Chem. Res. Toxicol., 14:975-987, 2001.

Rogers et al., Ionic Liquids—Solvents of the Furture?, Science., 302:792-793, 2003.

Sanchez et al., Density, Viscosity, and Surface Tension of Synthesis Grade Imidazolium, Pyridinium, and Pyrrolidinium Base Room Temperature Ionic Liquids, J. Chem. Eng. Data., 54:2803-2812, 2008.

Schneider et al., Green Bipropellants: Hydrogen-Rich Ionic Liquids that Are Hypergolic with Hydrogen Peroxide, Angew. Chem. Int. Ed., 50:5886-5888, 2011.

Schneider et al., Ionic Liquids as Hypergolic Fuels, Energy Fuels, 22:2871-2872, 2008.

Seddon, Ionic Liquids a taste of the future, Nature Materials, 2:363-365, 2003.

Siedle et al., Assignment of the 11B NMR Spectrum of the Tridecahydro Decaborate(1-) Ion, J. Inorg. Nucl. Chem., 33:3671-3676, 1971.

Sneddon et al., Structure of the B10H13-Ion, J. Chem. Soc. Chem. Commun., 474-475, 1972.

Spengler et al., Über den Zündverzug hypergoler Raketentreibstoffe, Brennstoff-Chemie, 4:43-50, 1965.

Wang et al., Boronium-Cation-Based Ionic Liquids as Hypergolic Fluids, Chem. Eur. J., 18:16931-16937, 2012.

Yang, Y., Determination of the thermal transport properties of ammonia borane and its thermolysis product (polyiminoborane) using the transient plane source technique, Hydrogen Energy, 37:5128-5136, 2012.

Zhang et al., Dicyanoborate-Based Ionic Liquids as Hypergolic Fluids, Angew. Chem. Int. Ed., 50:935-937, 2011.

Zhang et al., Ionic Liquieds as Hypergolic Fuels, Angew. Chem. Int. Ed., 50:9554-9562, 2011.

McCrary et al., Nonaborane and Decaborane Cluster Anions Can Enhance the Ignition Delay in Hypergolic Ionic Liquids and Induce Hypergolicity in Molecular Solvents, Inorganic Chemistry, 53:4770-4776, 2014.

Volkov et al. "Mechanochemical Synthesis in Chemistry of Cluster Systems." Chemistry for Sustainable Development, 2005, 13, 155-163.

Williams et al. "Boron Hydride Derivatives. Part IX. The Reaction of Decaborane with Ammonia." Journal of the Chemical Society, 1963, 5816-5824.

* cited by examiner t = 0 ms    6 ms    97 ms    148 ms t = 0 ms     t = 8 ms     t = 61 ms     t = 96 ms t = 0 ms     3 ms     177 ms     219 ms

HYPERGOLIC SALTS WITH BORANE CLUSTER ANIONS

CROSS-REFERENCE TO RELATED APPLICATIONS

This application claims benefit of U.S. Provisional Application No. 61/837,404, filed Jun. 20, 2013, which is hereby incorporated herein by reference in its entirety.

STATEMENT REGARDING FEDERALLY SPONSORED RESEARCH

This invention was made with Government Support under Grant FA9550-10-1-0521 awarded by the U.S. Air Force Office of Scientific Research and National Defense, Science, and Engineering Graduate Fellowship. The Government has certain rights in the invention.

FIELD

The subject matter disclosed herein generally relates to hypergolic salts with borane cluster anions and propellant or explosive formulations comprising borane cluster anions and methods of forming the salts and formulations. The subject matter disclosed herein further relates to hypergolic borane cluster anions as a trigger additive for combustible solvents or as an additive for hypergol to shorten ignition delay.

BACKGROUND

In a bipropellant rocket engine, the hypergolic fuel and the oxidizer can be stored as two separate components, yet ignite spontaneously on contact, effectively eliminating the need for an igniter. Ever since this discovery, the hunt has been on for new hypergols that yielded improved properties over each predecessor. Currently, the state of the art propellants, hydrazine and its derivatives are volatile, carcinogenic, and reactive, but offer reliable performance. Some of the other propellant such as Rocket Propellant-1 (RP-1) that are less toxic require the use of liquid oxygen, a substance that is very difficult to maintain in the liquid state.

Thus, there exists a need for methods and compositions that overcome some of problems in the art of bipropellant, a few of which are aforementioned. Disclosed herein are compositions and methods that meet these and other needs.

SUMMARY

In accordance with the purposes of the disclosed materials, compounds, compositions, articles, devices, and methods, as embodied and broadly described herein, the disclosed subject matter, in one aspect, relates to compositions and methods for preparing propellant or explosive formulations comprising borane cluster anions and using them. Further, the subject matter disclosed herein relates to propellant or explosive formulations comprising borane cluster anions as trigger additives for combustible solvents or ionic liquids, and methods of obtaining and using them. In a further aspect, the disclosed subject matter relates to propellant or explosive formulations comprising borane cluster anions as additive for hypergol to shorten ignition delay of the hypergol and the method of using the formulation. In an additional aspect, the disclosed subject matter relates propellant or explosive formulations comprising borane cluster anions formed in situ in an ionic liquid and the method of forming and using the formation.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

DETAILED DESCRIPTION

Figure 1:
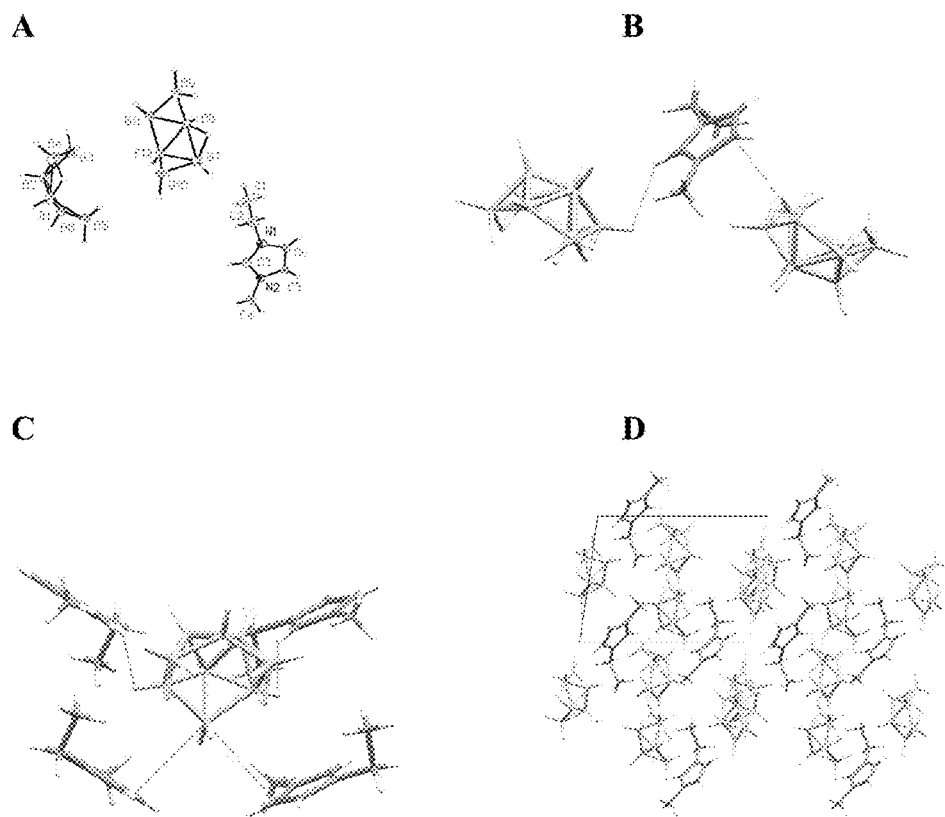
FIG. 1 shows illustrations of crystal structures of $[C_2mim][B_9H_{14}]$ (A) 50% probability ellipsoid ORTEP diagram of the asymmetric unit; (B) short (<sum of the van der Waals radii) contacts around the cation; (C) short contacts around the anion, and (D) packing diagram.

The materials, compounds, compositions, articles, devices, and methods described herein may be understood more readily by reference to the following detailed description of specific aspects of the disclosed subject matter and the Examples included therein and to the Figures.

Before the present materials, compounds, compositions, formulations, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not. For example, the phrase "X is an optional component in the formulation" means that X may or may not be present in the formulation and that the description includes both formulations where X is present and where X is not present.

References in the specification and concluding claims to parts by weight of a particular element or component in a composition denotes the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the composition.

A weight percent (wt. %) of a component, unless specifically stated to the contrary, is based on the total weight of the formulation or composition in which the component is included.

Chemical Definitions

As used herein, the term "hypergolic composition" is contemplated to include a composition that ignites spontaneously when it comes into contact with an oxidizer.

The term "ion," as used herein, refers to any molecule, portion of a molecule, cluster of molecules, molecular complex, moiety, or atom that contains a charge (positive, negative, or both (e.g., zwitterions)) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, etc.

The term "anion" is a type of ion and is included within the meaning of the term "ion". An "anion" is any molecule, portion of a molecule (e.g., zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion". A "cation" is any molecule, portion of a molecule (e.g., zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —OA$^1$ where A$^1$ is alkyl as defined above.

The term alkoxylalkyl as used herein is an alkyl group that contains an alkoxy substituent and can be defined as -A$^1$-O-A$^2$, where A$^1$ and A$^2$ are alkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C=C(A$^3$A$^4$) are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula NA$^1$A$^2$A$^3$, where A$^1$, A$^2$, and A$^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O$^-$.

The term "ester" as used herein is represented by the formula —OC(O)A$^1$ or —C(O)OA$^1$, where A$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula A$^1$OA$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula A$^1$C(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiA$^1$A$^2$A$^3$, where A$^1$, A$^2$, and A$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. Throughout this specification "S(O)" is a short hand notation for S=O.

The term "sulfonyl" is used herein to refer to the sulfo-oxo group represented by the formula —S(O)$_2$A$^1$, where A$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "sulfone" as used herein is represented by the formula A$^1$S(O)$_2$A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" as used herein is represented by the formula A$^1$S(O)A$^2$, where A$^1$ and A$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Reference will now be made in detail to specific aspects of the disclosed materials, compounds, compositions, formulations, articles, and methods, examples of which are illustrated in the accompanying Examples and Figures.

Materials and Compositions

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or can be prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). In general, the materials can be derived from a natural source or from a synthetic source.

Also, disclosed herein are materials, compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds, compositions or formulations may not be explicitly disclosed, each is specifically contemplated and described herein. For example, if a composition is disclosed and a number of modifications that can be made to a number of components of the composition are discussed, each and every combination and permutation that are possible are specifically contemplated unless specifically indicated to the contrary. Thus, if a class of components A, B, and C are disclosed as well as a class of components D, E, and F and an example of a composition A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, formulations or steps in methods of making and using the disclosed compositions or formulations. Thus, if there are a variety of additional steps that can be performed it is understood that each of these additional steps can be performed with any specific aspect or combination of aspects of the disclosed methods, and that each such combination is specifically contemplated and should be considered disclosed.

Hypergolic Compositions

Boranes (B$_x$H$_y$) have been explored as potential fuels, but due to their high volatility, toxicity, reactivity with many organic solvents, and solid product formation (B$_2$O$_3$) upon oxidation, much of the interests shifted away. The reduction potential locked in a B—H bond, therefore, has yet to be exploited in propellants and safe explosives. Stable borane cluster anions such as [B$_{10}$H$_{13}$]$^-$ and [B$_9$H$_{14}$]$^-$ generated from relatively stable borane, nido-decaborane (B$_{10}$H$_{14}$), have been reported as early as 1960's and 70's (see for example Hawthorne et al., *J. Am. Chem. Soc.* 1960, 82, 1825-1829; Greenwood et al., *J. Chem. Soc., Dalton Trans.* 1972, 986-989; and Hawthorne et al., *J. Am. Chem. Soc.* 1958, 80, 754-754, the disclosures of which are incorporated by reference in their entireties for their teachings of boranes). The salts can be synthesized based on proton transfer mechanisms including direct acid-base reaction, salt metathesis, or through hydroxide intermediate. Detailed NMR and X-ray studies of the borane cluster anion [B$_{10}$H$_{13}$]$^-$ have been reported in Siedle et al., *J. Inorg. Nucl. Chem.* 1971, 33, 3671-3676 and Sneddon et al., *J. Chem. Soc., Chem. Commun.* 1972, 474-475, the disclosures of which are incorporated by reference in their entireties for their teachings of borane clusters. Borane clusters such as anion [B$_{10}$H$_{12}$]$^{2-}$ and vinyl decaborane-polyester copolymer binder were disclosed in U.S. Pat. Nos. 3,050,361 and 3,967,989 respectively. Neutral boranes have been used in borane and ionic liquid mixtures to decrease ignition delay, or the time needed for ignition to occur, of hypergolic fuels as reported in Gao et al., *J. Mater. Chem.* 2012, 22, 11022-11025, where up to 50:50 mixtures for any effect is required. Boranes recently have also been reported to be used in the production of propellants as discussed in Yang, *Hydrogen Energy* 2012, 37, 5128-5136. However, there is no report of hypergolicity in literature and none of the existing literature discloses or suggests using stable borane cluster anions such as $[B_{10}H_{13}]^-$ and $[B_9H_{14}]^-$ with an oxidizer in propellants and safe explosives.

Ionic liquids (ILs, a class of salts arbitrarily defined to possess melting points below 100° C. as discussed in Rogers and Seddon, *Science* 2003, 302, 792-793 and Seddon, *Nature Materials* 2003, 2, 363-365) containing the dicyanamide anion have been previously reported to be hypergolic with nitric acid in Schneider et al., *Energy Fuels* 2008, 22, 2871-2872. Dicyanamide ILs offer several safety advantages over traditional propellants, such as low or negligible volatility, high thermal stability. However, key properties, such as heat of combustion, ignition delay, and low temperature viscosity, did not match up to the performance of hydrazine. Thus, the development of new hypergolic ILs burgeoned through the design of new anions which exhibited improved performance, such as nitrocyanamide, dicyanoborohydride, and aluminum borohydride anions among others. Beyond the deficient energetic properties, the current platform of hypergolic ILs must also be extensively purified and dried in order to retain hypergolicity, which limits reliability under practical circumstances.

Disclosed herein are hypergolic compositions that are air stable and hypergolic in the presence of water. In some examples, the hypergolic composition comprises a cation and a hypergolic borane cluster anion derived from decaborane. In some examples, the borane cluster anion can be incorporated into a combustible solvent or existing hypergol. For example, the borane cluster anion can be used as a trigger additive for a combustible solvent to form the hypergolic composition. The borane cluster anion can also, for example, be mixed with an existing hypergol as an additive to shorten the ignition delay of the hypergol. In some examples, the hypergolic composition can be formulated with an oxidizer to form a propellant or explosive formulation. The hypergolic compositions disclosed herein are surprisingly hypergolic when nitric acid having a concentration of 70% to 100% is used as an oxidizer.

Also disclosed herein are hypergolic salts. The hypergolic salts disclosed herein can comprise a single cation and a single anion, which is derived from decaborane, wherein the salts are air-stable and hypergolic in the presence of water. In some examples, the hypergolic salts can ignite in the presence of water. In some examples, the anion derived from decaborane can comprise a decaborane cluster ($[B_{10}H_{13}]^-$), a nonaborane cluster ($[B_9H_{14}]^-$), or a combination thereof.

In some examples, the cation of can comprise an alkyl or aromatic heterocyclic cation, a quaternary ammonium cation, or quaternary phosphonium cation. In some examples, the cation can be cyclic, such as an azolium cation, a cyclic ammonium cation, or an imidazolium cation. In some examples, the cation can comprise a single heteroatom wherein a sufficient number of substituted or unsubstituted linear or branched alkyl units are attached to the heteroatom such that a positively charged species is formed. For example, the cation can comprise $C_n$ alkyl-methylimidazolium [$C_n$mim], where n is an integer of from 1 to 8. In some examples, the cation can comprise $C_{1-4}$ alkyl-methylimidazolium [$C_{1-4}$mim]. In some examples, the cation can comprise an allyl methylimidazolium ion, [Amim]. Other nonlimiting examples of cationic units include imidazoles, pyrazoles, thiazoles, isothiazoles, azathiozoles, oxothiazoles, oxazines, oxazolines, oxazaboroles, dithiozoles, triazoles, selenozoles, oxahospholes, pyrroles, boroles, furans, thiophenes, phospholes, pentazoles, indoles, indolines, oxazoles, isothirazoles, tetrazoles, benzofurans, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, and quinoxalines.

The following are examples of heterocyclic units that are suitable for forming a cyclic heteroalkyl cation unit of suitable ILs or ion-containing solvents.

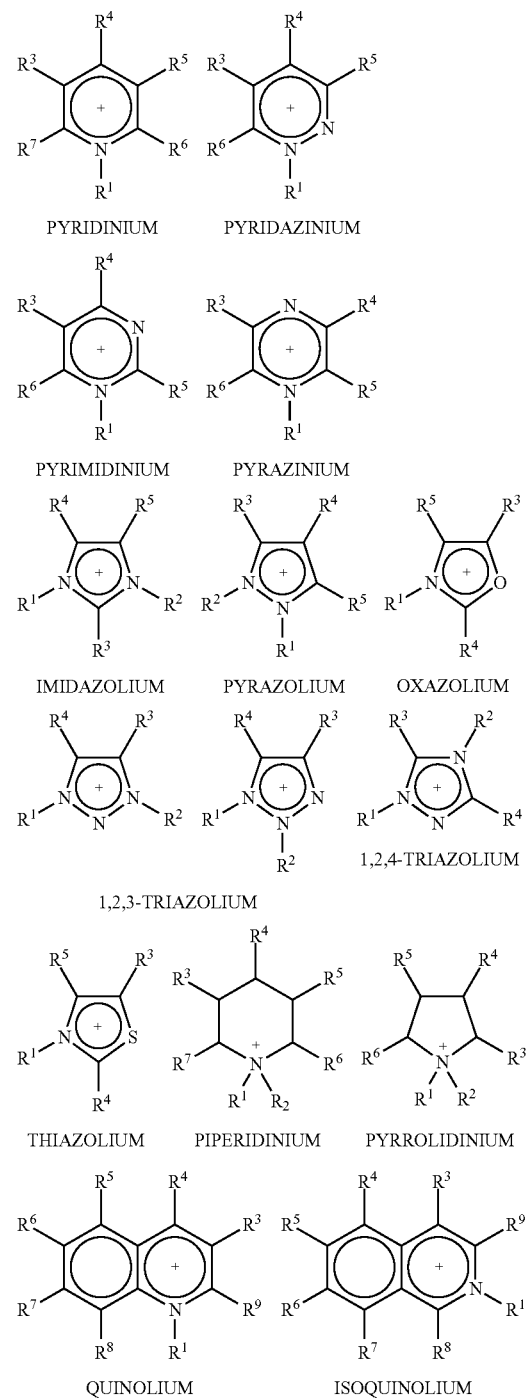

-continued

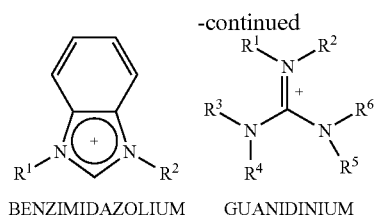

BENZIMIDAZOLIUM    GUANIDINIUM

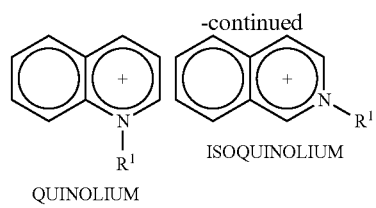

QUINOLIUM    ISOQUINOLIUM where each $R^1$ and $R^2$ is, independently, hydrogen, a substituted or unsubstituted linear, branched, or cyclic $C_1$-$C_6$ alkyl, a substituted or unsubstituted linear, branched, or cyclic $C_1$-$C_6$ alkoxy, or substituted or unsubstituted linear or branched, $C_1$-$C_6$ alkoxyalkyl; each $R^3$, $R^4$, $R^5$, $R^6$, $R^7$, $R^8$, and $R^9$ is, independently, hydrogen, substituted or unsubstituted linear, branched, or cyclic $C_1$-$C_6$ alkyl, substituted or unsubstituted linear, branched, or cyclic $C_1$-$C_6$ alkoxy, or substituted or unsubstituted linear or branched, $C_1$-$C_6$ alkoxyalkyl. In some examples, both $R^1$ and $R^2$ groups are $C_1$-$C_4$ alkyl, with one being methyl, and $R^3$-$R^9$, when present, are H. Exemplary $C_1$-$C_6$ alkyl groups and $C_1$-$C_4$ alkyl groups include methyl, ethyl, propyl, iso-propyl, butyl, sec-butyl, iso-butyl, pentyl, iso-pentyl, hexyl, 2-ethylbutyl, 2-methylpentyl, and the like. Corresponding $C_1$-$C_6$ alkoxy groups contain the above $C_1$-$C_6$ alkyl group bonded to an oxygen atom that is also bonded to the cation ring. It is to be noted that there are two isomeric 1,2,3-triazoles. In some examples, all R groups not required for cation formation can be H.

In some examples, all R groups that are not required for cation formation (i.e., those other than $R^1$ and $R^2$ for compounds other than the imidazolium, pyrazolium, and triazolium cations shown above) are H. Thus, the cations shown above can have a structure that corresponds to a structures shown below, wherein $R^1$ and $R^2$ are as described before.

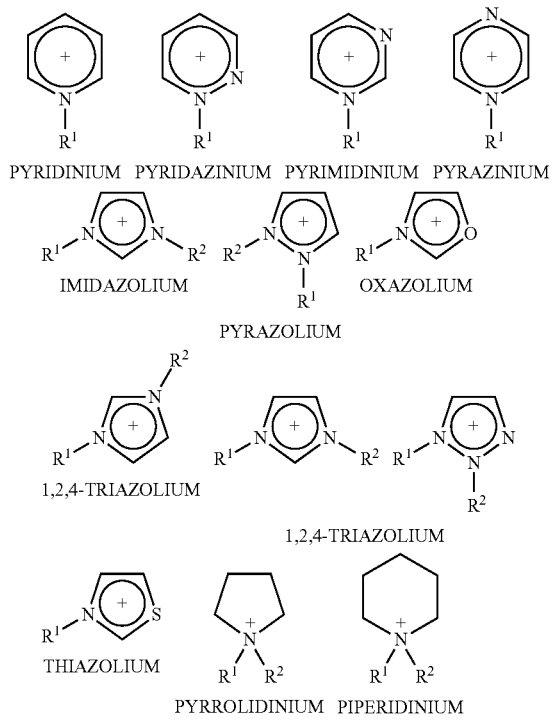

Exemplary cations are illustrated below wherein $R^1$, $R^2$, and $R^3$-$R^5$, when present, are as defined before. In protic cations, which can be used herein, either $R^1$ or $R^2$ is hydrogen. In aprotic cations, $R^1$ and $R^2$ are not hydrogen and are, e.g., a substituted or unsubstituted linear, branched, or cyclic $C_1$-$C_6$ alkyl, a substituted or unsubstituted linear, branched, or cyclic $C_1$-$C_6$ alkoxy, or substituted or unsubstituted linear or branched, $C_1$-$C_6$ alkoxyalkyl.

The following is a description of the short hand method used throughout the specification for referring to the imidazolium-based cations disclosed herein. The template:

[$C_n$mim]

represents the cation portion wherein $C_n$ represent an alkyl or substituted alkyl moiety having n number of carbon atoms. The term "mim" refers to "methyl substituted imidazolium." Referring to the generic imidazolium formula:

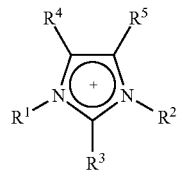

wherein $R^3$, $R^4$, and $R^5$ are each hydrogen, can also be written as follows:

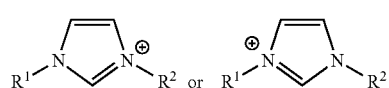

wherein either nitrogen can be depicted as having a positive charge. By the convention used herein the methyl group of "mim" refers to the $R^1$ moiety and the $C_n$ substituent is the $R^2$ moiety. Therefore [$C_2$mim] represents a cation having the formula:

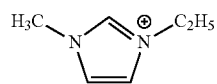

which can be equally well represented by the formula:

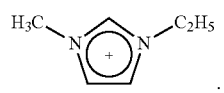

Of the cations that contain a single five-membered ring free of fusion to other ring structures, an imidazolium cation that corresponds in structure to Formula A is also suitable, wherein $R^1$, $R^2$, and $R^3$-$R^5$, are as defined before.

(A)

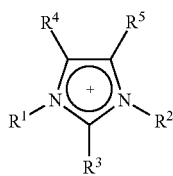

In some examples of Formula A, $R^3$ can be H. In some examples of Formula A, $R^4$ can be H. In some examples of Formula A, $R^5$ can be H. In some examples of Formula A, $R^3$-$R^5$ can each be H. In some examples of Formula A, $R^1$ can comprise a $C_1$-$C_{16}$ alkyl group or a $C_1$-$C_{16}$ alkoxyalkyl group. In some examples of Formula A, $R^2$ can comprise a $C_1$-$C_{16}$ alkyl group or a $C_1$-$C_{16}$ alkoxyalkyl group. In some examples, the cation of Formula A can comprise an N,N-1,3-di-($C_1$-$C_{16}$ alkyl)-substituted-imidazolium ion; i.e., an imidazolium cation of Formula A wherein $R^3$-$R^5$ are each H, and $R^1$ and $R^2$ are each independently a $C_1$-$C_{16}$ alkyl group or a $C_1$-$C_{16}$ alkoxyalkyl group. In some examples, the cation can comprise a 1-($C_1$-$C_{16}$-alkyl)-3-(methyl)-imidazolium [$C_n$-mim, where n=1-16] cation and the anion can comprise a halogen anion. In further examples of Formula A, $R^1$ can be hydrogen, as in a protic cation. In some examples of Formula A, $R^3$-$R^5$ are each hydrogen, $R^2$ is methyl, $R^1$ is a $C_1$-$C_{16}$-alkyl group or a $C_1$-$C_{16}$ alkoxyalkyl group, and the cation can comprise a compound of Formula B.

(B)

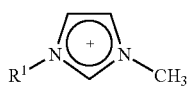

In some examples, the optionally substituted imidazolium cation can comprise a 1-alkyl 3-methylimidazolium cation, including, for example, 1-ethyl-3-methylimidazolium, 1-butyl 3-methylimidazolium, 1-pentyl 3-methylimidazolium, 1-hexyl 3-methyl imidazolium, 1-heptyl 3-methylimidazolium, 1-octyl 3-methylimidazolium, 1-nonyl 3-methylimidazolium, 1-decyl 3-methylimidazolium, and 1-hexadecyl 3-methylimidazolium.

In still other examples, the cation can comprise a pyridinium cation or a pyrrolidinium cation as shown in the Formula (C) and Formula (D) respectively.

(C)

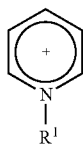

(D)

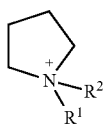

where $R^1$ is H, in a protic cation, or a substituted or unsubstituted linear, branched, or cyclic $C_1$-$C_6$ alkyl, a substituted or unsubstituted linear, branched, or cyclic $C_1$-$C_6$ alkoxy, or substituted or unsubstituted linear or branched, $C_1$-$C_6$ alkoxyalkyl, and $R^2$ is a substituted or unsubstituted linear, branched, or cyclic $C_1$-$C_6$ alkyl, a substituted or unsubstituted linear, branched, or cyclic $C_1$-$C_6$ alkoxy, or substituted or unsubstituted linear or branched, $C_1$-$C_6$ alkoxyalkyl.

In some examples, the cation can comprise an ammonium cation, such as shown in the formula below:

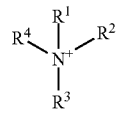

AMMONIUM wherein $R^1$, $R^2$, $R^3$, and $R^4$, when present, are independently a $C_1$-$C_{18}$ alkyl group or a $C_1$-$C_{18}$ alkoxyalkyl group.

In some examples, the cation can comprise a phosphonium cation, such as shown in the formula below:

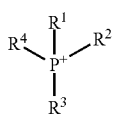

PHOSPHONIUM wherein $R^1$, $R^2$, $R^3$, and $R^4$, when present, are independently a $C_1$-$C_{18}$ alkyl group or a $C_1$-$C_{18}$ alkoxyalkyl group.

In some examples, the hypergolic composition can ignite spontaneously upon contact with nitric acid that has a concentration of 70% or greater (e.g., 75% or greater, 80% or greater, 85% or greater, 90% or greater, 95% or greater, 98% or greater, 99% or greater, 99.5% or greater, or 99.8% or greater). In some examples, the hypergolic salt can ignite spontaneously upon contact with nitric acid that has a concentration of 100% or less (e.g., 99.8% or less, 99.5% or less, 99% or less, 98% or less, 95% or less, 90% or less, 85% or less, 80% or less, or 75% or less). In some examples, the hypergolic salt can ignite spontaneously upon contact with nitric acid that has a concentration in the range from 70% to 100% (e.g., 75% to 99%, 70 to 85%, 85% to 100%, 70% to 75%, 75% to 80%, 80% to 85%, 85% to 90%, 90% to 95%, 95% to 100%, 75% to 95%, 75% to 85%, 85% to 95%, or 80% to 90%).

In some examples, the ignition delay of the hypergolic composition with an oxidizer, such as nitric acid, is less than 12 ms (e.g., less than 11 ms, less than 10 ms, less than 9 ms, less than 8 ms, less than 7 ms, less than 6 ms, less than 5 ms, less than 4 ms, less than 3 ms, less than 2 ms, or less than 1 ms).

An effective amount of the hypergolic salt can be mixed with a combustible substance as a trigger additive to render the combustible substance hypergolic. For example, the combustible substance can be a combustible solvent, such as tetrahydrofuran, acetone, acetonitrile, ethyl acetate, or a combination thereof, and the hypergolic salt can be suspended or dissolved in the combustible solvent. In some examples, the combustible substance can comprise a combustible ionic liquid. In some examples, the concentration or amount of the hypergolic salt in the combustible substance or solvent can be at least 0.01 mg/mL (e.g., at least 1 mg/mL, at least 5 mg/mL, at least 10 mg/mL, at least 20 mg/mL, at least 30 mg/mL, at least 40 mg/mL, at least 50 mg/mL, at least 60 mg/mL, at least 70 mg/mL, at least 80 mg/mL, or at least 90 mg/mL). In some examples, the concentration or amount of the hypergolic salt in the combustible substance or solvent can be 100 mg/mL or less (e.g., 90 mg/mL or less, 80 mg/mL or less, 70 mg/mL or less, 60 mg/mL or less, 50 mg/mL or less, 40 mg/mL or less, 30 mg/mL or less, 20 mg/mL or less, 10 mg/mL or less, or 1 mg/mL or less). In some examples, examples, the concentration or amount of the hypergolic salt in the combustible substance or solvent can be in the range of from 0.01 to 100 mg/mL (e.g., 0.1 to 50 mg/mL, 50 to 100 mg/mL, 0.1 to 25 mg/mL, 25 to 50 mg/mL, 50 to 75 mg/mL, 75 to 100 mg/mL, 0.1 to 90 mg/mL, 0.2 to 50 mg/mL, 0.5 to 25 mg/mL, 1 to 10 mg/mL, 10-90 mg/mL, 20-80 mg/mL, 30-70 mg/mL, 40-60 mg/mL, 0.1 to 5 mg/mL, or 5 to 10 mg/mL).

When introduced or incorporated as an additive into an existing hypergol, the hypergolic salt disclosed herein can effectively shorten the ignition delay of the existing hypergol. Existing or known hypergols include, for example, rock propellant-1 (RP-1), kerosene, furfuryl alcohol, hydrazine, hypergolic ionic liquid, methane, or a combination thereof. In some examples, the hypergolic salt can be suspended or dissolved in the hypergol. In some examples, the concentration or amount of the hypergolic salt in the hypergol can be at least 0.01 mg/mL (e.g., at least 1 mg/mL, at least 5 mg/mL, at least 10 mg/mL, at least 20 mg/mL, at least 30 mg/mL, at least 40 mg/mL, at least 50 mg/mL, at least 60 mg/mL, at least 70 mg/mL, at least 80 mg/mL, or at least 90 mg/mL). In some examples, the concentration or amount of the hypergolic salt in the hypergol can be 100 mg/mL or less (e.g., 90 mg/mL or less, 80 mg/mL or less, 70 mg/mL or less, 60 mg/mL or less, 50 mg/mL or less, 40 mg/mL or less, 30 mg/mL or less, 20 mg/mL or less, 10 mg/mL or less, or 1 mg/mL or less). In some examples, examples, the concentration or amount of the hypergolic salt in the hypergol can be in the range of from 0.01 to 100 mg/mL (e.g., 0.1 to 50 mg/mL, 50 to 100 mg/mL, 0.1 to 25 mg/mL, 25 to 50 mg/mL, 50 to 75 mg/mL, 75 to 100 mg/mL, 0.1 to 90 mg/mL, 0.2 to 50 mg/mL, 0.5 to 25 mg/mL, 1 to 10 mg/mL, 10-90 mg/mL, 20-80 mg/mL, 30-70 mg/mL, 40-60 mg/mL, 0.1 to 5 mg/mL, or 5 to 10 mg/mL). In some examples, the hypergolic salt can shorten the ignition delay of the hypergol by at least 50% (e.g., at least 60%, at least 70%, at least 80%, at least 85%, or at least 90%). In some examples, prior to adding the borane cluster anions salt additive, some of the hypergol does not ignite spontaneously on contact with concentrated nitric acid. RP-1, for example, is currently paired with liquid oxygen, which must be kept under pressure and cooled in order to be condensed to the liquid phase. By incorporating the borane cluster anion salts described herein, nitric acid can be used as a replacement oxidizer to ignite RP-1. Nitric acid, for example, does not need to be constantly replaced and has safer and cheaper storage conditions. This can eliminate the need to pressurize and regularly replace the liquid oxygen, allowing for the use of a cheaper and safer alternative oxidizer. The borane cluster anion additive therefore can expand the possibility of the existing hypergols to pair with alternative oxidizers such as concentrated nitric acid, for example from 70 to 100% nitric acid.

The hypergolic borane cluster anions can, in some examples, be generated in situ. For example, when decaborane is added directly to an ionic liquid (IL), a metathesis reaction can occur to generate borane cluster anions to replace some of the anions of the hypergolic IL. The newly generated borane cluster anions can render the IL hypergolic or, in the case of a hypergolic IL, shorten the ignition delay of the hypergolic IL. The cation of the ionic liquid can, for example, be an alkyl or aromatic heterocyclic cation, qua- ternary ammonium cation, quaternary phosphonium cation, or a combination thereof, as discussed above. In some examples, the anion of the ionic liquid can be hypergolic. Hypergolic anions in ionic liquids for example include, but are not limited to, dicyanamide anion (DCA), nitrocyanamide anion (NCA), dicyanoborate anion, and a combination thereof. In some examples, the molar ratio of the ionic liquid and the borane cluster anions formed can be 1000:1 or less (e.g., 900:1 or less, 800:1 or less, 700:1 or less, 600:1 or less, 500:1 or less, 400:1 or less, 300:1 or less, 200:1 or less, 100:1 or less, 50:1 or less, 25:1 or less, 10:1 or less, 5:1 or less, or 2:1 or less). In some examples, the molar ratio of the ionic liquid and the borane cluster anions formed can be 1:1 or more (e.g., 2:1 or more, 5:1 or more, 10:1 or more, 25:1 or more, 50:1 or more, 100:1 or more, 200:1 or more, 300:1 or more, 400:1 or more, 500:1 or more, 600:1 or more, 700:1 or more, 800:1 or more, or 900:1 or more). In some examples, the molar ratio of the ionic liquid and the borane cluster anions formed can be in the range of 1000:1 to 1:1 (e.g., 1000:1 to 500:1, 500:1 to 1:1, 1000:1 to 750:1, 750:1 to 500:1, 500:1 to 250:1, 250:1 to 1:1, or 750:1 to 250:1).

Propellant or Explosive Formulations

Also disclosed herein are propellant or explosive formulations, such as a bipropellant formulation. In some examples, the propellant or explosive formulation can comprise a hypergolic composition and an oxidizer, wherein the hypergolic composition and oxidizer are separate prior to use. In some examples, the hypergolic composition can comprise a cation and a hypergolic borane cluster anion derived from decaborane. In some examples, the hypergolic composition is air stable and hypergolic in the presence of water.

In some examples of the propellant or explosive formulations, the anion derived from decaborane is decaborane cluster anion ($[B_{10}H_{13}]^-$), nonaborane cluster anion ($[B_9H_{14}]^-$), or a combination thereof.

In some examples of the propellant or explosive formulations, the cation can comprise an alkyl or aromatic heterocyclic cation, quaternary ammonium cation or quaternary phosphonium cation, such as any of those described in detail above.

In some examples of the propellant or explosive formulations, the oxidizer comprises nitric acid having a concentration of from 70% to 100%.

In some examples of the propellant or explosive formulations, the hypergolic composition further comprises a combustible solvent. In some examples, an effective amount of the borane cluster anion is suspended or dissolved in the combustible solvent. In some examples, the combustible solvent can comprise tetrahydrofuran, acetone, acetonitrile, ethyl acetate, a combustible ionic liquid or a combination thereof. In some examples, the concentration or amount of the hypergolic salt in the combustible solvent is from 0.01 to 100 mg/mL.

In some examples of the propellant or explosive formulations, the hypergolic composition further comprises a hypergol. In some examples, the hypergol can be selected from rock propellant-1, kerosene, furfuryl alcohol, hydrazine, hypergolic ionic liquid, methane, or a combination thereof. In some examples, the borane cluster anion can be mixed in the hypergol. In some examples, the concentration or amount of the negative borane cluster anion in the hypergol can be from 0.01 to 100 mg/mL.

In some examples of the propellant or explosive formulations, the negative borane cluster anion can shorten the ignition delay of the hypergol by at least 80%.

In some examples of the propellant or explosive formulations, the borane cluster anion can be formed in situ in an ionic liquid having a cation and an anion. In some examples, the cation of the ionic liquid can be an alkyl or aromatic heterocyclic cation, quaternary ammonium cation, or quaternary phosphonium cation, such as those described in more detail above. In some examples, the anion of the ionic liquid can be hypergolic. In some examples, the anion of the ionic liquid can be dicyanamide anion (DCA), nitrocyanamide anion, or dicyanoborate anion. In some examples, the molar ratio of the ionic liquid and the borane cluster anion can be from 1000:1 to 1:1.

In some examples, the hypergolic salt can be formulated with from 70% to 100% nitric acid as bipropellant fuel or explosive. In some examples, the hypergolic salt can serve as a solid bipropellant in combination with nitric acid. In some examples, the hypergolic compositions described above that comprise the hypergolic salt as trigger additive can be formulated with 100% nitric acid as the bipropellant fuel or explosive. In some examples, a hypergol doped with the hypergolic salt, as described above, can be formulated with an alternative oxidizer, such as 100% nitric acid, that was not previously used with the hypergol, as a bipropellant.

Methods of Making and Use

Also provided herein are methods of making hypergolic salts. In some examples, the method of making can comprise mixing decaborane with a base to form a hypergolic salt that comprises a single positively charged cation and a single negatively charged anion derived from the decaborane.

In some examples, the anion derived from the decaborane can comprise decaborane cluster anion ($[B_{10}H_{13}]^-$), nonaborane cluster anion ($[B_9H_{14}]^-$), or a combination thereof.

In some examples, the base can comprise an alkyl or aromatic heterocycle, tertiary amine, tertiary phosphine to form the cation as alkyl or aromatic heterocyclic cation, quaternary ammonium cation or quaternary phosphonium cation, such as those described in detail above.

In some examples, the decaborane mixed with the base can form a metal salt and the method can further comprise reacting the metal salt with an ionic liquid (IL) comprising a single positively charged cation and a halogen anion to form the hypergolic ionic liquid salt that comprises the single positively charged cation derived from the IL and the single negatively charged anion derived from the decaborane and a metal halide.

In some examples, the method can further comprise obtaining the hypergolic salt through extraction.

In some examples, the method can further comprise washing the hypergolic salt with ether to remove any remaining, unreacted decaborane and base.

In some examples, the hypergolic salt can be purified via recrystallization.

The hypergolic salts disclosed herein can, for example, be synthesized via proton transfer. In some examples, a direct acid base reaction was used (Reaction A), where decaborane can directly react with a base (B) to form a decaborane cluster anion and a protonated base ([H—B]).

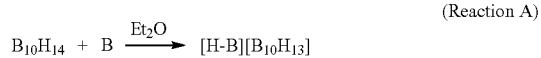

(Reaction A)

In some examples, decaborane can react directly with a base ([Cat][OH]) that has an organic cation ([Cat]) and a hydroxide anion to form a decaborane cluster anion salt with the organic cation and water (Reaction B).

$B_{10}H_{14}+[Cat][OH]\rightarrow[Cat][B_{10}H_{13}]+H_2O$ (Reaction B)

In some examples, decaborane can first react with a hard base (MOH) to produce borane cluster anions, which in turn can react with an organic salt ([Cat]X) that has an organic cation [Cat] and a halogen anion X to form a borane cluster anion salt with the organic cation and salt MX (Reaction C). In some examples, the organic salt comprises an ionic liquid and the cation of the borane salt is formed from the ionic liquid.

(Reaction C)

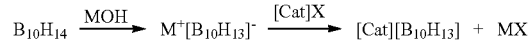

When the decaborane is treated with a hydroxide anion in the presence of water, such as in Reactions B and C, a nonaborane anion $[B_9H_{14}]^-$ can also be formed through the generation of gaseous hydrogen and the loss of sodium borate, as illustrated in Examples 3 and 7 below. The anion of the hypergolic salt generated from reactions B and C above, therefore, can be a decaborane cluster anion ($[B_{10}H_{13}]^-$), nonaborane cluster anion ($[B_9H_{14}]^-$), or a combination thereof, depending on the reaction conditions used.

The cations ([H—B] or [Cat]) in reactions A-C above have been described in detail in the above sections. The corresponding base is used to produce the cation as specified in reactions A-C above. For example, an alkyl or aromatic heterocycle, tertiary amine, or tertiary phosphine base can be used to form an alkyl or aromatic heterocyclic cation, quaternary ammonium cation or quaternary phosphonium cation. In some examples, the base can comprise an azole, a cyclic amine, or an imidazole. In some examples, the borane cluster anions described herein are stable in water. In some examples, the hypergolic salt formed can be isolated from the reaction mixture through extraction or filtration. In some examples, the hypergolic salts can be washed with ether to remove unreacted decaborane and base. In some examples, the hypergolic borane salt can be purified via recrystallization.

Also provided herein are methods of use of the hypergolic salts disclosed herein. Also provided herein are methods of use of the hypergolic compositions disclosed herein. In some examples, the methods of use can comprise using the hypergolic salts or hypergolic compositions as propellants or explosives. In some examples, the hypergolic salts can be used as a solid propellant. In some examples, the methods of using the hypergolic salts or hypergolic compositions as propellants or explosives comprises combining the hypergolic salt or hypergolic composition with from 70% to 100% nitric acid.

By way of non-limiting illustration, examples of certain embodiments of the present disclosure are given below.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions.

All chemicals used were of analytical grade, purchased from Sigma-Aldrich (Milwaukee, Wis.), and used without further purification unless otherwise noted.

Example 1: Formation of Protic Nido-Decaborane Salts

Formation of protic decaborane cluster anion salts from a base, such as a tertiary amine, generally referred to as synthetic route A, is presented in this example. A solution of nido-decaborane in diethyl ether was added drop-wise to a stirred solution of triethylamine in an equimolar ratio. Upon the addition, a pale yellow powder precipitated. The resulting solid was recrystallized by dissolving the separated product in ethyl acetate, followed by the slow addition of diethyl ether, which resulted in pale yellow crystalline needles with a melting point of 98° C.

In the $^1$H NMR, the newly formed N—H proton was visible as a triplet at 6.7 ppm. Additionally, the methylene carbon attached directly to the amine was present as a doublet of a quartet, further indicating protonation. For the $[B_{10}H_{13}]^-$ anion, both the terminal B—H and bridging B—H hydrogen atoms appear shifted upfield, and it also included the loss of a single bridging hydrogen atom. $^{11}$B NMR further supported the formation of only the $[B_{10}H_{13}]^-$ anion through the formation of 4 unique doublets at 7.2, 2.8, −4.8, and −14.8 ppm (2:1:5:2 intensity) relative to an external standard of $BF_3.OEt_2$ that all became singlets upon decoupling to $^1$H, which matches previous $^{11}$B results for this anion reported in Hofmann et al., *Inorg. Chem.* 1998, 37, 5557-5565 and Siedle et al., *J. Inorg. Nucl. Chem.* 1971, 33, 3671-3676. IR spectroscopy revealed a large shift in the B—H stretch, which indicated reduction and deprotonation based on the results of similar anionic species as reported in Chin et al., *J. Am. Chem. Soc.* 1994, 116, 9359-9360. Finally, the pXRD revealed a crystalline pattern not associated with the nido-decaborane starting material, supporting the formation of protic borane salt $[H-TEA][B_{10}H_{13}]$.

Following the procedure outlined above for the synthesis of $[H-TEA][B_{10}H_{13}]$, additional protic borane salts are synthesized and listed in Table 1.

TABLE 1

| [Cation]$^+$ | Characterization | Literature Values | Observations |
|---|---|---|---|
| 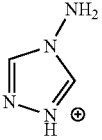 [4-AT] | IR | n.a. | Clear Glass Hypergolic w/ WFNA −<3 ms ID |
|  [Py] | IR, pXRD | n.a. | Orange Powder, Amorphous |
| 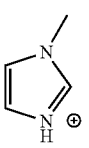 [Me-Im] | IR, pXRD | n.a. | Bright Yellow powder, amorphous |
| 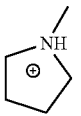 [1-Me-Pyrr] | IR | n.a. | Yellow wax |
| 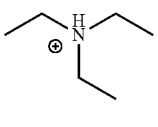 [TEA] | IR, pXRD | mp = 98° C[1] (dec) Elemental Analysis[1] | Bright Yellow powder, crystalline |

TABLE 1-continued

| [Cation]+ | Characterization | Literature Values | Observations |
|---|---|---|---|
| 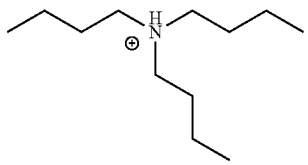 [TBA] | IR, pXRD | Elemental Analysis[1] | Bright Yellow powder, crystalline |

[1] Hawthorne, M. F.; Pitochelli, A. R.; Strahm, R. D.; Miller, J. J. J. Am. Chem. Soc. 1960, 82, 1825-1829.

Example 2: Formation of Aprotic Nido-Decaborane Salts

Borane cluster anions can also be generated from bases such as quaternary amine cations to form aprotic salts. The synthesis of an aprotic salt with a borane cluster anion from the base of a quaternary amine cation is referred to as synthetic route B (or Reaction B) herein. When the borane cluster anion is generated from a hard base, such as sodium hydroxide, followed by reaction with a halogen salt of a quaternary cation, the synthetic route is generally referred to as route C (or Reaction C) herein. Aprotic salts synthesized through route B are listed in Table 2 below. Aprotic salts synthesized through route C are listed in Table 3 below.

TABLE 2

| [Cation]+ | Characterization | Literature Values | Observations |
|---|---|---|---|
| Me–N(Me)(Me)–Me [N1111] | IR, pXRD | mp > 250° C.* Elemental Analysis* | Bright Yellow powder, crystalline |
| Me–N(Me)(Me)–C16H33 [N11116] | IR, pXRD | n.a. | Bright Yellow powder, crystalline |
| Et–N(Et)(Et)–Et [N2222] | IR, pXRD | Elemental Analysis* | Bright Yellow powder, crystalline |
| Bu–N(Bu)(Bu)–Bu [N4444] | IR, pXRD | Elemental Analysis* | Bright Yellow powder, crystalline |
| Bu–P(Bu)(Bu)–Bu [P4444] | IR, pXRD, SCXRD | Elemental Analysis* | Light Yellow powder, crystalline |

TABLE 2-continued

| [Cation]+ | Characterization | Literature Values | Observations |
|---|---|---|---|
| 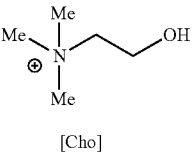 [Cho] | IR, pXRD | n.a. | White powder |

*Hawthorne, M. F.; Pitochelli, A. R.; Strahm, R. D.; Miller, J. J. J. Am. Chem. Soc. 1960, 82, 1825-1829.

TABLE 3

| [Cation]+ | Characterization | Literature Values | Observations |
|---|---|---|---|
| Me–N(Me)(Me)–Me [N1111] | IR, pXRD | mp > 250 ° C[1] Elemental Analysis* | Bright Yellow powder, crystalline |
| Me-imidazolium-Et [EMIM] | IR, pXRD | n.a. | White solid |
| Me-imidazolium-Bu [BMIM] | IR, pXRD | n.a. | Bright Yellow waxy solid |
| Me-pyrrolidinium-Bu [BM Pyrr] | IR, pXRD | n.a. | Bright Yellow waxy solid |

*Hawthorne, M. F.; Pitochelli, A. R.; Strahm, R. D.; Miller, J. J. J. Am. Chem. Soc. 1960, 82, 1825-1829.

Example 3: Formation of Imidazolium Salts with Borane Cluster Anions

Reaction of nido-decaborane with a hard base, such as NaOH, resulted primarily in the formation of $[B_9H_{14}]^-$ through the generation of gaseous hydrogen and the loss of sodium borate based on reactivity summarized in the scheme below.

$$B_{10}H_{14} + 2NaOH + 2H_2O \rightarrow Na[B_9H_{14}] + Na[B(OH)_4] + H_2$$

The reaction has been previously reported in Benjamin et al., *J. Am. Chem. Soc.* 1963, 85, 2674-2675. The imidazolium cation is used in this example to react further with the borane cluster anion to form stable salts.

A solution of nido-decaborane in anhydrous ethanol was added drop-wise to a stirred, equimolar solution of NaOH in aqueous ethanol. The clear solution immediately turned bright yellow and a small amount of gas was released. After the release of gas ceased, an aqueous solution of [C$_2$mim]Cl or [C$_4$mim]Cl was added to the solution. The bright yellow solution was stirred for 5 minutes and ethyl acetate was utilized to extract the salt. The organic layers were combined and solvent removed via slow evaporation to obtain a yellow powder and a bright yellow viscous emulsion when [C$_2$mim]$^+$ and [C$_4$mim]$^+$ were utilized as the counter-ion, respectively.

Single crystals of [C$_2$mim][arachno-B$_9$H$_{14}$] were obtained through the slow evaporation of a mixture of ethyl acetate and n-butanol. The crystal structure as well as the packing diagram of [C$_2$mim][arachno-B$_9$H$_{14}$] are illustrated in FIG. 1. As show in FIG. 1, a hydrogen bond was present between the C2H of the imidazolium cation and a hydride present on the open face of the anion, which dominates the crystal structure packing diagram. In an article by Bould et al., *J. Am. Chem. Soc.* 2002, 124, 7429-7439, K[B$_9$H$_{14}$] has been reported to have a {3×µ-H, 2×endo} conformation (3 bridging hydrogen atoms and two hydrogen atoms that are in the endo conformation) along the open face of the [B$_9$H$_{14}$]$^-$ anion. [C$_2$mim][B$_9$H$_{14}$] was found to be in the {2×µ-H, 3×endo} arrangement due to π stabilization provided by the [C$_2$mim]$^+$ cation to the third endo position. The $^{11}$B NMR of [C$_2$mim][B$_9$H$_{14}$] displayed three doublets at −24.2, −21.0, and −8.7 ppm, and the $^1$H NMR displayed 5 rapidly exchanging B—H hydrogen atoms along the open face of the anion at −1.50 ppm and two separate overlapping 1:1:1:1 quartets between 0.5 and 2.0 ppm; these spectra matched closely to those reported in Bould et al.

As discussed above, [C$_4$mim]Cl produced a bright yellow viscous emulsion. It appears that using only one equivalent of NaOH resulted in a mixture of both the [B$_{10}$H$_{13}$]$^-$ and [B$_9$H$_{14}$]$^-$ anions, as indicated by the observation of both sets of boron peaks in the $^{11}$B spectrum of [C$_4$mim][B$_9$H$_{14}$]$_m$ [B$_{10}$H$_{13}$]$_n$, where m and n are equivalents of [B$_9$H$_{14}$]$^-$ to [B$_{10}$H$_{13}$]$^-$ anions in the formula. Additional synthetic procedures were attempted with higher NaOH:nido-decaborane ratios, which resulted in a higher relative ratio of [B$_9$H$_{14}$]$^-$ to [B$_{10}$H$_{13}$]$^-$ in the isolated emulsion. However, a high level of anionic purity was not obtained using the [C$_4$mim]$^+$ counter-ion.

Example 4 Reactivity of Nonaborane and Decaborane Salts

Both the nonaborane and the decaborane salts were tested for reactivity with a variety of oxidizers. The resulting ignition was monitored with a Redlake MotionPro Y3 at 1000 frames/s. In the case of the solid salts [H-TEA][B$_{10}$H$_{13}$] and [C$_2$mim][B$_9$H$_{14}$], a small portion (~10-20 mg of salt) was placed on a 10 cm watch glass. An aliquot (2-3 drops) of each oxidizer was dropped directly onto the portion of nonaborane or decaborane salt and the resulting ignition monitored. As the [C$_4$mim]$^+$ salt was an emulsion at room temperature, a typical hypergolic drop test was possible. A typical hypergolic drop test was reported in for example Schneider et al., *Energy Fuels* 2008, 22, 2871-2872; McCrary et al., *Chem. Commun.* 2012, 48, 4311-4313; and McCrary et al., *Angew. Chem. Int. Ed.* 2012, 51, 9784-9787, which are incorporated by reference herein in their entireties for their teachings of hypergolic compositions and tests. Here, 10 µL of the liquid fuel was carefully added to a vial containing 500 µL of the selected oxidizer. The three oxidizers chosen for study were white fuming nitric acid (WFNA, 100% nitric acid), inhibited red fuming nitric acid (IRFNA, 90% nitric acid), and 70% nitric acid (NA). The values for ignition delay (ID) were measured as the time from when the fuel initially contacts the oxidizer until ignition was observed (measured in ms).

Figure 2:
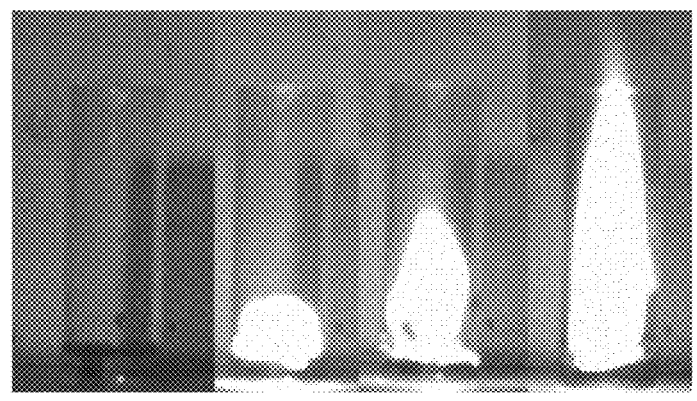
FIG. 2 shows the hypergolic ignition of $[C_4mim][B_9H_{14}]_m[B_{10}H_{13}]_n$ upon the contact with WFNA: (A) 0 ms—drop hitting the surface of WFNA, (B) 3 ms—resulting flame, (C) 50 ms—ongoing flame, and (D) 120 ms—the highest flame height observed.

Upon contact with WFNA, all three salts ignited with IDs less than 1 ms; essentially displaying instantaneous hypergolic ignition. The hypergolic ignition of [C$_4$mim][B$_9$H$_{14}$]$_m$[B$_{10}$H$_{13}$]$_n$ upon the contact with WFNA was recorded in FIG. 2. As shown in FIG. 2, the [C$_4$mim]$^+$ salt displayed immediate ignition upon contact with WFNA yielding the green flame typical in the combustion of boron hydride compounds reported in Dequasie, *The Green Flame: Surviving Government Secrecy*. American Chemical Society: Washington, D.C., 1991. Here, the high reactivity of the [C$_4$mim]$^+$ salt demonstrated that this class of salts did not require extensive purification and could essentially be extracted and utilized directly from the aqueous phase after the evaporation of the organic phase without further treatment. Additionally, all salts ignited upon contact with both IRFNA and NA, resulting in the visual observation of a green flame upon ignition, which is a drastic improvement over the required use of WFNA with traditional hypergolic ILs. Other, more dilute, oxidizers were attempted, such as 1 M nitric acid, 30% H$_2$O$_2$ and 50% H$_2$O$_2$, but did not result in ignition.

Example 5: Reactivity of Nonaborane and Decaborane Salts as Trigger Additives The nonaborane and decaborane salts were used as "trigger" additives to promote the ignition of combustible solvents in this example. Small portions (~10-20 mg) of each salt were placed on a 10 cm watch glass. Approximately 10 mL of a solvent was used to dissolve the salts. Both polar protic (ethanol, methanol, and water) and polar aprotic solvents (THF and ethyl acetate) were utilized. Chlorinated solvents were avoided due to the potential hazard of the generation of shock sensitive explosives. Non-polar solvents, such as diethyl ether and hydrocarbon based fuels, did not solubilize any of the fuel additives tested here, but this solubility could potentially be improved with proper cation selection. After the additive was dissolved, several drops of oxidizer were dropped directly into the solution, and the resulting ignition was monitored with the high speed camera as previously mentioned.

Figure 3:
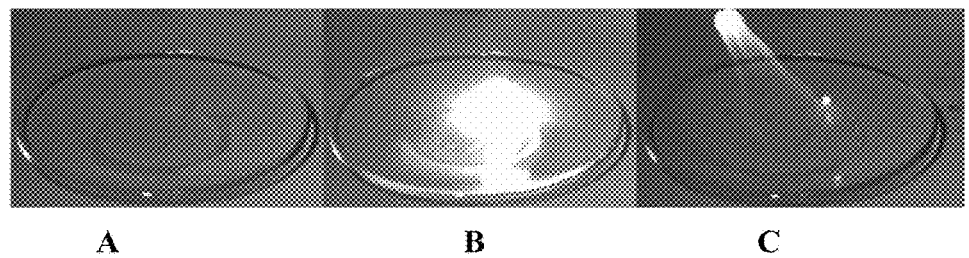
FIG. 3 shows the $[C_2mim][B_9H_{14}]$ as a trigger additive to induce hypergolicity in EtOAc: (A) 0 ms—initial contact with oxidizer, (B) 2 ms—hypergolic ignition of $[C_2mim][B_9H_{14}]$, (C) dilute green flame visible in the ignition of EtOAc.

By dissolving salts derived from nido-B$_{10}$H$_{14}$ directly into polar aprotic solvents, they acted as trigger additives to induce hypergolicity upon contact with WFNA. As seen in FIG. 3, a solution of [H-TEA][B$_{10}$H$_{13}$] in ethyl acetate (EtOAc) ignited at 2 ms upon contact with an oxidizer. This ignition provided enough thermal energy to ignite EtOAc, which burned for several hundred ms. All three salts exhibited similar behavior in both EtOAc and THF. Lower concentrations of nitric acid did not result in ignition. In each ignition, a green flame was observed in both the vigorous initial ignition and during the resulting combustion of the solvent.

However, when a protic polar solvent was utilized instead, such as an alcohol, no trigger activity was observed. The protic nature of the solvent appears to stabilize the borane cluster anions to prevent spontaneous ignition upon contact with an oxidizer. Although salts containing either or both the $[B_9H_{14}]^-$ and $[B_{10}H_{13}]^-$ anions were insoluble in water, it did not prevent ignition. Floating any of the 3 compounds on water still resulted in the ignition of the trigger additives upon contact with an oxidizer. Water would act to sequester the flames, but the fact that the ignition was possible in the presence of water would allow for flexibility when utilized in rocket propellant formulations.

In summary, the results provided here indicated that $[B_{10}H_{13}]^-$ and/or $[B_9H_{14}]^-$ act as trigger additives to induce hypergolicity in benign solvents, such as EtOAc and THF. The ignition delays are still under 3 ms. As an anionic mixture of $[B_{10}H_{13}]^-$ and $[B_9H_{14}]^-$ still ignited as a neat compound, in solution and in the presence of water, extensive purification of these compounds was not required for trigger activity.

Example 6: Nonaborane and Decaborane Salts as Additives for Hypergol

This example demonstrates nonaborane and decaborane salts can act as a faster source of ignition in current hypergol formulations, allowing for practical use with current rocket propellant formulations. Nonaborane and decaborane salts were incorporated into known hypergolic ILs as additives and the values for ignition delay were compared with those of the neat samples. 1-Butyl-3-methylimidazolium dicyanamide ([C$_4$mim][DCA]), 1-allyl-3-methylimidazolium dicyanamide ([Amim][DCA]), and 1-methyl-4-amino-1,2,4-triazolium dicyanamide ([MAT][DCA]) were synthesized through a metathesis reaction between the respective halide precursor and silver dicyanamide in methanol, as described in Schneider et al., *Energy Fuels* 2008, 22, 2871-2872 and McCrary et al., *Chem. Commun.* 2012, 48, 4311-4313.

In order to incorporate a reduced borane species into these hypergolic ILs, nido-$B_{10}H_{14}$ was added directly to the ILs in 1000:1, 100:1, and 10:1 molar ratios of IL:decaborane. Before the addition of nido-$B_{10}H_{14}$, each IL was dried to be less than 500 ppm of $H_2O$ as measured by Karl-Fischer titration through high vacuum drying and 3 independent freeze-thaw cycles. The calculated amount of nido-$B_{10}H_{14}$ was placed in a pre-weighed 2 dram vial. The IL was drop-wise added to the vial and the resulting mixture was vortex mixed for 15 seconds. Upon addition, [C$_4$mim][DCA] and [Amim][DCA] turned a bright orange shade while [MAT][DCA] turned a cloudy orange hue, with increasing darkness seen with higher loadings in all cases. In all mixtures, visible gas formation was present along with a dramatic increase in viscosity, which were both directly related to the amount of added nido-$B_{10}H_{14}$. Black precipitates formed upon standing and were removed by centrifugation. With [DCA]$^-$ acting as a base for the generation of anionic borane species, H-DCA is believed to quickly trimerize to form melamine derivatives that precipitate out of the liquid phase, as reported in Chingin et al., *Angew. Chem. Int. Ed.* 2011, 50, 8634-8637.

The solubilized boranes were characterized by NMR spectroscopy using a neat capillary tube surrounded by an external locking solvent, DMSO-d6. In all cases, the only boron species present was identified to be the $[B_9H_{14}]^-$ based on three doublets that corresponded to the peaks assigned earlier to $[C_2mim][B_9H_{14}]$. A blue shift of the B—H stretch was also observed in the IR upon the formation of the $[B_9H_{14}]^-$ anion. Additionally, a 1:1 sample of [MAT][DCA]:nido-$B_{10}H_{14}$ mixture was prepared, which resulted in an amorphous solid with a B—H stretch at 2888 cm$^{-1}$ that matched closely to the B—H bond stretching frequency in $[C_2mim][B_9H_{14}]$ (2885 cm$^{-1}$). As a result, the addition of nido-$B_{10}H_{14}$ directly to [DCA]$^-$ based ILs resulted in the in situ formation of $[B_9H_{14}]^-$.

Figure 4:
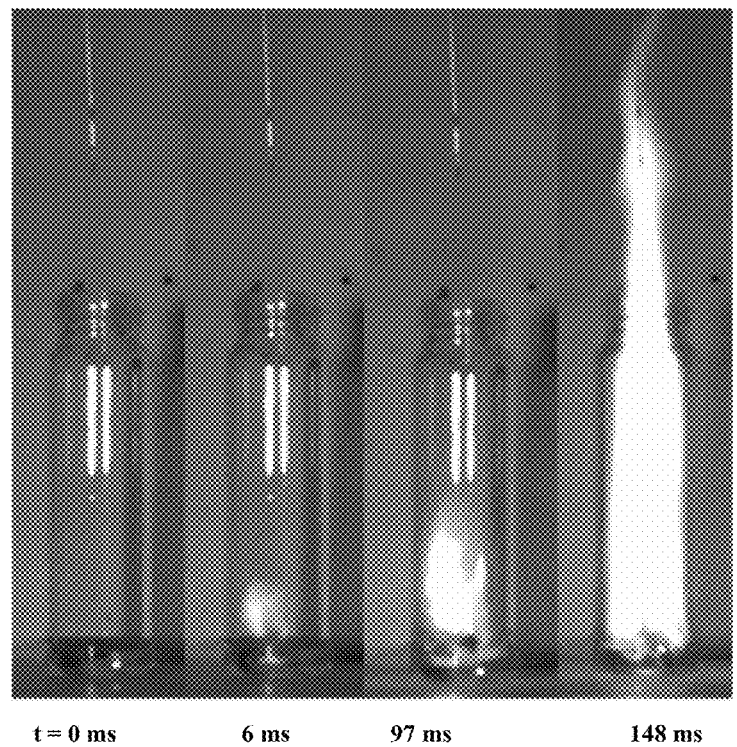
FIG. 4 shows that $[B_9H_{14}]$ incorporated as additive shortens ignition delay for $[C_4mim][DCA]$.
Figure 5:
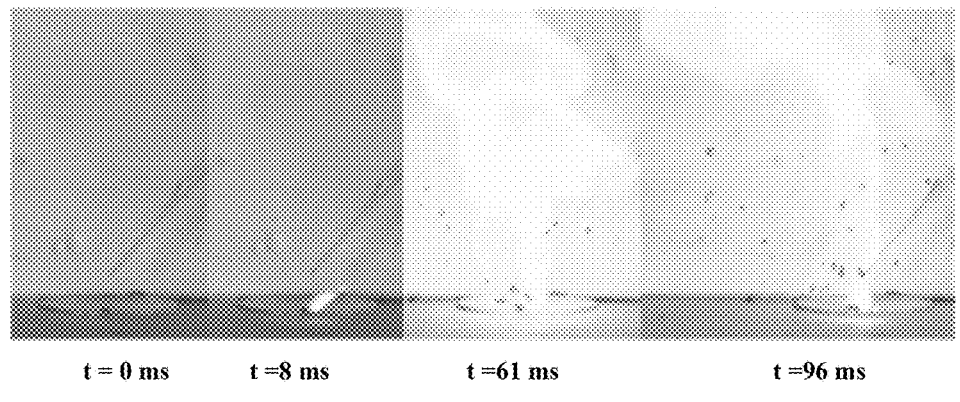
FIG. 5 shows that $[B_9H_{14}]$ incorporated as additive shortens ignition delay for $[MAT][DCA]$.
Figure 6:
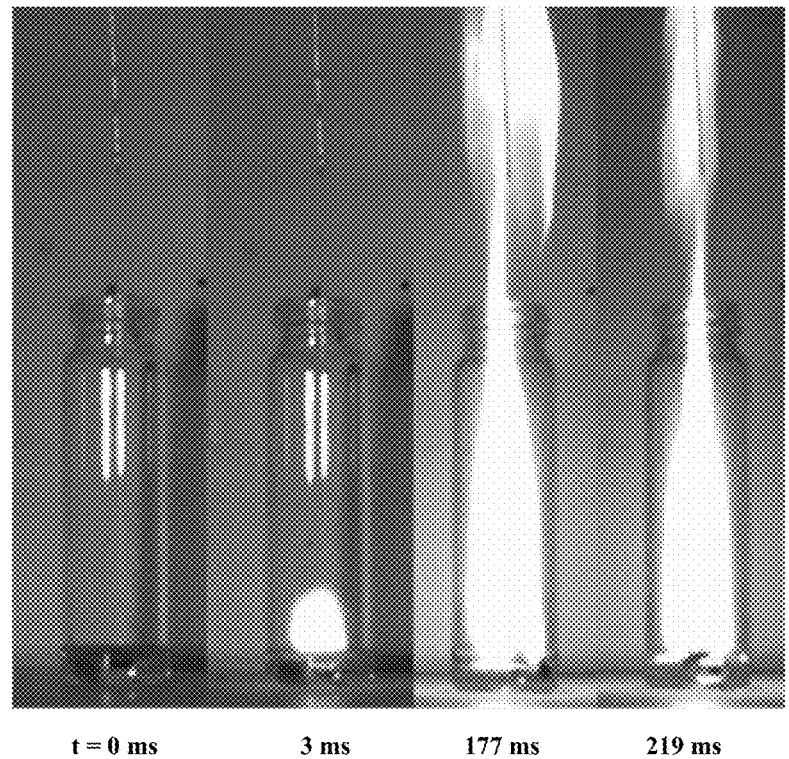
FIG. 6 shows that $[B_9H_{14}]$ incorporated as additive shortens ignition delay for $[MAT][DCA]$.

Ignition tests for the ILs containing $[B_9H_{14}]^-$ were conducted utilizing a standard IL hypergolic drop test set up as described above with WFNA and the results are listed in Table 4 below. The ignition delays for [C4mim][DCA], [MAT][DCA] and [Amim][DCA] incorporated with 10:1 mol ratio $[B_9H_{14}]^-$ were recorded as described above and shown in FIGS. 4, 5, and 6 respectively.

TABLE 4

| Ionic Liquid | Ignition delay (ms) Molar ratio of IL: $[B_9H_{14}]^-$ | | | |
|---|---|---|---|---|
| | Neat | 1000:1 | 100:1 | 10:1 |
| [C$_4$mim]  [DCA] | 48(4) | 58(3) | 42(2) | 5$^a$ |
| [MAT]  [DCA] | 39(2) | 53(6) | 31(1) | 11(4)$^b$ |
| [Amim]  [DCA] | 35(5) | 33(4) | 30(6) | 4(1) |

$^a$Due to high viscosity of sample only one ignition delay was obtained
$^b$Due to high viscosity of sample, the drop test was performed in a watch glass instead of a vial
$^c$Values in parenthesis denote standard deviation of three averaged tests Flames with a light green hue were observed upon ignition in all cases. At low 1000:1 loadings of $[B_9H_{14}]^-$, the ignition delay was slightly shortened in [Amim][DCA], but lengthened in all other ILs. As discussed in McCrary et al., *Angew. Chem. Int. Ed.* 2012, 51, 9784-9787, because the viscosity of the IL increased with the incorporation of $[B_9H_{14}]^-$, the lengthening of the ignition delay could be observed due to the high dependence of the viscosity upon the mixing of the fuel and oxidizer and as a result the ignition delay. However, at a 100:1 loading ratio the ignition delay was shortened in all three cases by between 15-20% even with the increase in viscosity observed. At a 10:1 loading of IL-[$B_9H_{14}$]$^-$, the increase in viscosity limited the ability to use a syringe to conduct the hypergolic drop test. The ID of [Amim][DCA] was shortened to 4 ms upon the addition of [$B_9H_{14}$]$^-$ at a 10:1 molar ratio. The ID of [MAT][DCA] and [$C_4$mim][DCA] improved to 11 and 5 ms respectively. Due to viscosity of the mixtures, drop tests for [MAT][DCA] were instead conducted in a watch glass with 10-20 mg of [MAT][DCA]. A single drop of WFNA was dropped directly onto the IL-mixture, which resulted in the ignition of the fuel with a bright green flame. Essentially, the incorporation of borane cluster anions directly into known hypergols acted as an ID enhancer that provided a quicker ignition in comparison to the neat ILs. The most promising IL mixture, the 10:1 ratio in [Amim][DCA], appeared to have a quicker ID (4 ms) than unsymmetrical dimethyl hydrazine (15 ms) while still being a free-flowing liquid.

In summary, the incorporation of these additives to known hypergols provided an ID enhancement to shorten the ID. The additive strategy demonstrated here is a dramatically different approach to increase the safety and performance of hypergolic bipropellants. The incorporation of an additive to serve as the trigger or fuse to induce hypergolic ignition of nearly any fuel, transforms common fuels into powerful rocket propellants.

Example 7: Formation of Arachno-Nonaborane Cluster Anions

Formation of [$B_9H_{14}$]$^-$ through the reaction of nido-decaborane with a hard base, such as NaOH with subsequent reaction with an ionic liquid is summarized in the scheme below.

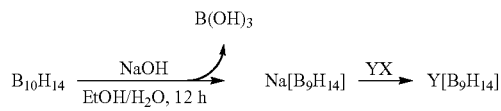

Where Y=[$C_2$mim]$^+$ or [Pyrr$_{14}$]$^+$
Where X=Cl$^-$

An aliquot of decaborane (3 mmol) dissolved in absolute ethanol is dropwise added to an aqueous solution of NaOH (3 mmol). Upon addition, the solution turned bright yellow, indicative of the formation of Na[$B_{10}H_{13}$] (and the reaction of H+ and OH−). Upon stirring for 12 h, bubbles formed and the solution turned clear. Through a series of reactions, Na[$B_9H_{14}$] and B(OH)$_3$ were formed. A solution of either [$C_2$mim]Cl or N-butyl-N-methyl-pyrrolidinium chloride ([Pyrr$_{14}$]Cl) in water was added dropwise to yield immediate precipitation of the respective Y[$B_9H_{14}$], i.e. [$C_2$mim][$B_9H_{14}$] or [Pyrr$_{14}$][$B_9H_{14}$]. The solid was collected by vacuum filtration and recrystallized with hot n-butanol.

Figure 7:
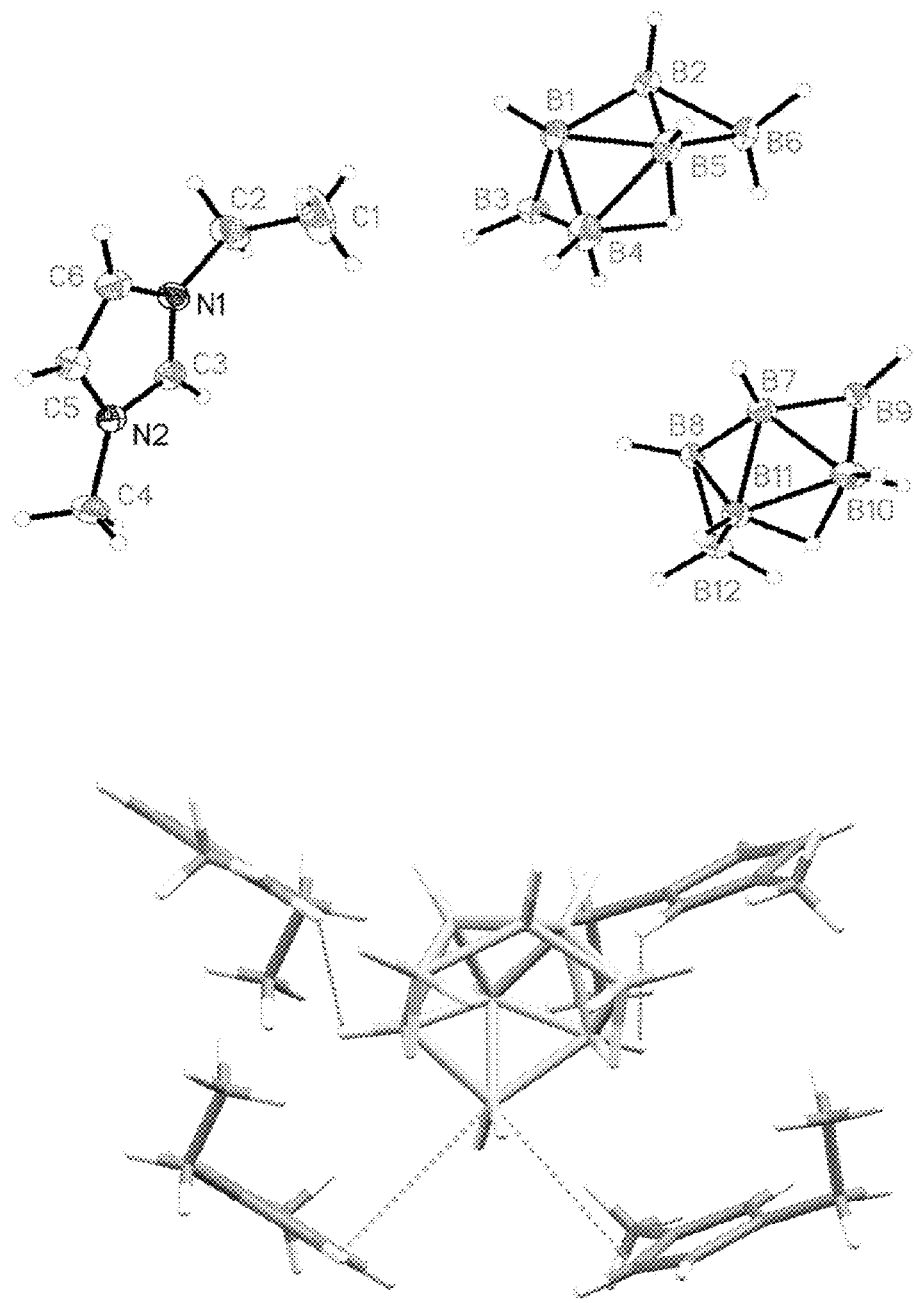
FIG. 7 shows the SCXRD of $[C_2mim][B_9H_{14}]$.
Figure 8:
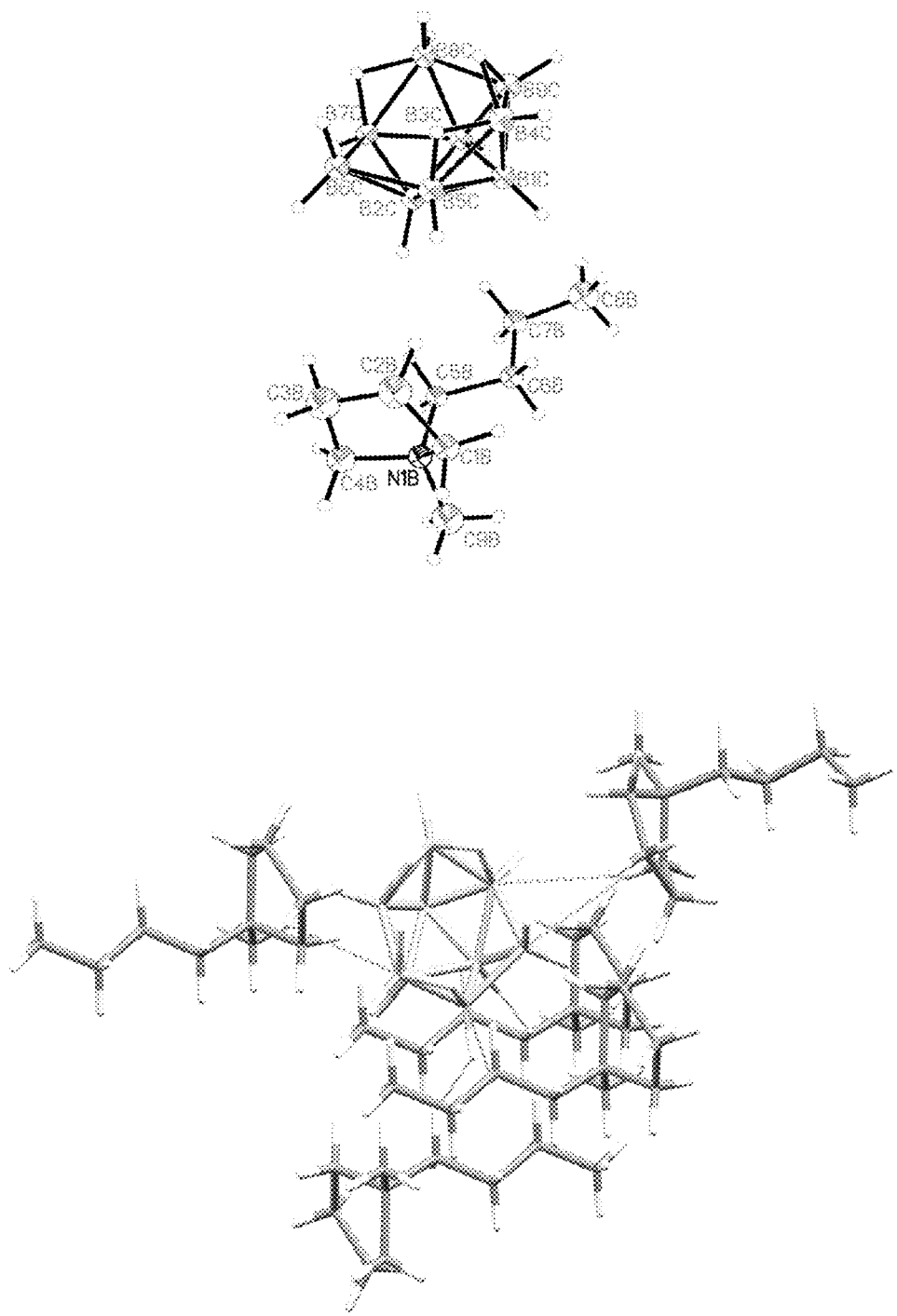
FIG. 8 shows the SCXRD $[Pyrr_{14}][B_9H_{14}]$.

The crystals of [$C_2$mim][$B_9H_{14}$] or [Pyrr$_{14}$][$B_9H_{14}$] were analyzed by Single Crystal X-Ray Diffraction (SCXRD), Powder X-Ray Diffraction (pXRD) and Differential scanning calorimetry (DSC) measurements. The SCXRD and DSC data are presented in FIGS. 7 to 10. Specifically, the SCXRD of [$C_2$mim][$B_9H_{14}$] shown in FIG. 7 revealed that there are 2 bridging hydrides with anions laying on an axis of symmetry, which does not match the anion confirmation reported in previous literature (see, Bould et al., *J. Am. Chem. Soc.* 2002, 124, 7429-7439; and Hofmann et al., *Inorg. Chem.* 1999, 38, 652-660). The SCXRD of [Pyrr$_{14}$][$B_9H_{14}$] in FIG. 8, however, showed there are 3 bridging hydrides and two endo spots that matches the 3 bridging hydride theory in literature. [$C_2$mim][$B_9H_{14}$] appears to be potential 3$^{rd}$ site π stabilized and has H—H dihydrogen bonding. [Pyrr$_{14}$][$B_9H_{14}$] appears to be not π stabilized and has less H—H dihydrogen bonding. The pXRDs of [$C_2$mim][$B_9H_{14}$] and [Pyrr$_{14}$][$B_9H_{14}$] have some similar peaks compared to the calculated pXRD data, although the calculated data contained significantly more distinct peaks, suggesting possible polymorphs in these salt structures.

The DSC measurements were carried out in three cycles and the results are plotted in FIG. 9 and FIG. 10 and summarized in Table 5 below.

TABLE 5

| | | Cycle 1 | Cycle 2 | Cycle 3 |
|---|---|---|---|---|
| [Pyrr$_{14}$][$B_9H_{14}$] | $T_c$ (° C.) | 35, 40 | 36, 39 | 36 |
| | $T_M$ (° C.) | 36, 49 | 37, 49 | 37, 52 |
| [$C_2$mim][$B_9H_{14}$] | $T_c$ (° C.) | | 16-17 | |
| | $T_M$ (° C.) | | 56 | |

Figure 9:
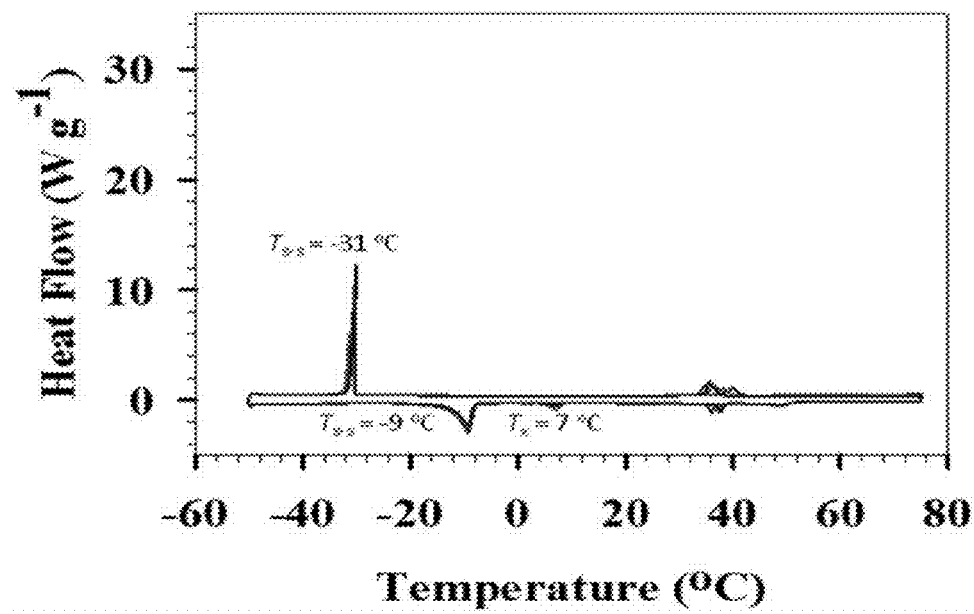
FIG. 9 shows the DSC of $[Pyrr_{14}][B_9H_{14}]$.
Figure 10:
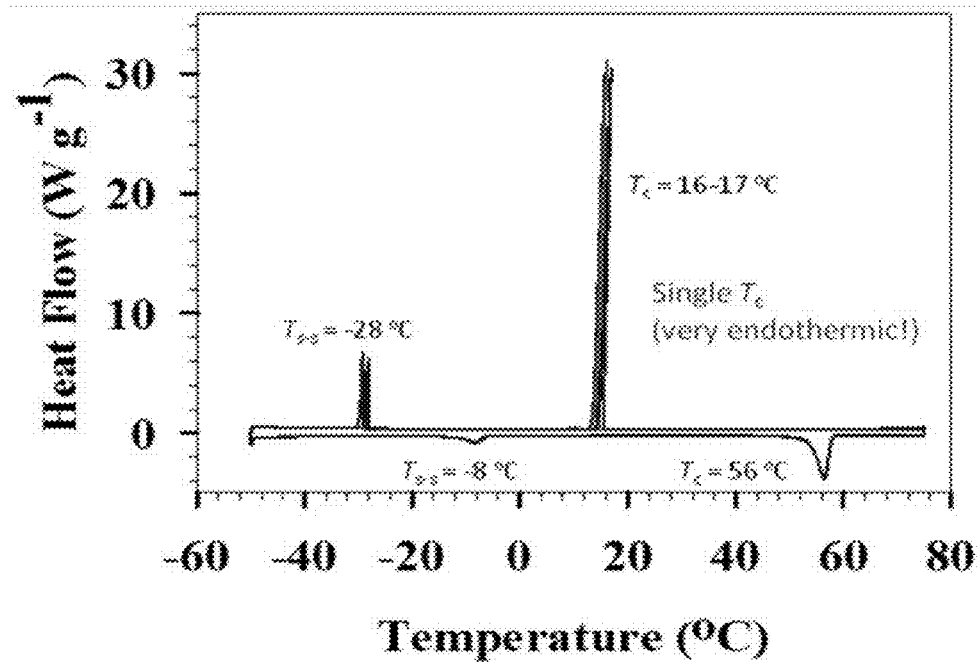
FIG. 10 shows the DSC of $[C_2mim][B_9H_{14}]$.

As shown in FIG. 9, because there is no stabilization from the cation in [Pyrr$_{14}$][$B_9H_{14}$], the $T_c$ and $T_M$ appeared as multiple small peaks. In contrast, as shown in FIG. 10, because there is it stabilization from the cation in [$C_2$mim][$B_9H_{14}$], the $T_c$ and $T_M$ appeared strong single peaks.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A hypergolic salt, comprising a single cation and a single anion derived from decaborane, wherein the hypergolic salt is air-stable and hypergolic in the presence of water,
wherein the anion derived from decaborane is a decaborane cluster anion ($[B_{10}H_{13}]^-$), nonaborane cluster anion ($[B_9H_{14}]^-$), or a combination thereof, and
wherein the cation is an alkyl or aromatic heterocyclic cation, quaternary ammonium cation or quaternary phosphonium cation.

2. The hypergolic salt of claim 1, wherein the cation is an azolium cation, a cyclic ammonium cation, or an imidazolium cation.

3. The hypergolic salt of claim 1, wherein the cation is

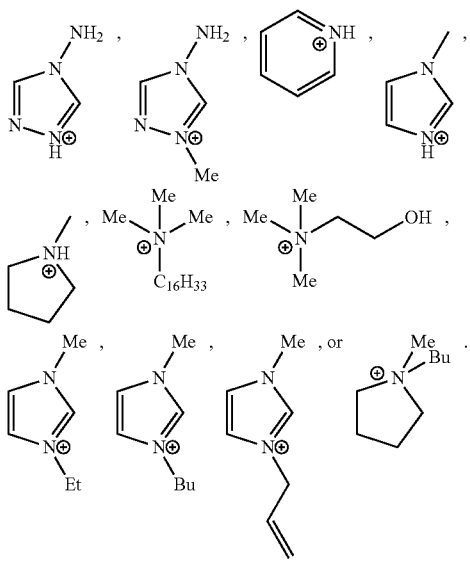

4. The hypergolic salt of claim 1, wherein the cation is a 1-ethyl-3-methylimidazolium cation.

5. The hypergolic salt of claim 1, wherein the cation is an N-butyl-N-methyl-pyrrolidinium cation.

6. The hypergolic salt of claim 1, wherein the hypergolic salt ignites spontaneously on contact with 70% to 100% nitric acid.

7. A method of use of the salt of claim 1 as a solid propellant, comprising combining the salt of claim 1 with 70% to 100% nitric acid.

8. A hypergolic composition comprising a hypergolic salt mixed in a combustible substance, wherein the hypergolic salt comprises a single positively charged cation and a single negatively charged anion derived from decaborane, and wherein the hypergolic salt is air-stable and hypergolic in the presence of water,
wherein the single negatively charged anion derived from decaborane is a decaborane cluster anion ($[B_{10}H_{13}]^-$), nonaborane cluster anion ($[B_9H_{14}]^-$), or a combination thereof, and
wherein the single positively charged cation is an alkyl or aromatic heterocyclic cation, quaternary ammonium cation or quaternary phosphonium cation.

9. The hypergolic composition of claim 8, wherein the combustible substance is tetrahydrofuran, acetone, acetonitrile, ethyl acetate, combustible ionic liquid or a combination thereof and the hypergolic salt is suspended or dissolved in the combustible substance.

10. The hypergolic composition of claim 8, wherein the combustible substance is a hypergol comprising rock propellant-1, kerosene, furfuryl alcohol, hydrazine, hypergolic ionic liquid, methane, or a combination thereof and the hypergolic salt is suspended or dissolved in the hypergol.

11. The hypergolic composition of claim 8, wherein the concentration of the hypergolic salt in the combustible substance is from 0.01 to 100 mg/mL.

12. The hypergolic composition of claim 8, wherein the hypergolic salt shortens the ignition delay of the combustible substance by 80% or more.

13. The hypergolic composition of claim 8, wherein the combustible substance is an ionic liquid comprising a cation and an anion and the hypergolic salt is formed in situ in the ionic liquid.

14. The hypergolic composition of claim 13, wherein the cation of the ionic liquid is an alkyl or aromatic heterocyclic cation, quaternary ammonium cation, or quaternary phosphonium cation.

15. The hypergolic composition of claim 14, wherein the anion of the ionic liquid is hypergolic.

16. The hypergolic composition of claim 15, wherein the anion of the ionic liquid is a dicyanamide anion (DCA), nitrocyanamide anion, or dicyanoborate anion.

17. The hypergolic composition of claim 13, wherein the molar ratio of the ionic liquid and the hypergolic salt is from 1000:1 to 1:1.

18. A propellant or explosive formulation, comprising the hypergolic composition of claim 8 and an oxidizer, wherein the hypergolic composition and oxidizer are separate prior to use.

* * * * *

UNITED STATES PATENT AND TRADEMARK OFFICE
CERTIFICATE OF CORRECTION

PATENT NO. : 10,099,967 B2
APPLICATION NO. : 14/310375
DATED : October 16, 2018
INVENTOR(S) : Parker D. McCrary et al.

Page 1 of 1

It is certified that error appears in the above-identified patent and that said Letters Patent is hereby corrected as shown below:

In the Claims

In Claim 9 at Column 30, Line 17, the term "sub stance" should read --substance--.

Signed and Sealed this
Twenty-fifth Day of December, 2018

Andrei Iancu
*Director of the United States Patent and Trademark Office*